United States Patent
Henley

(10) Patent No.: US 11,052,240 B2
(45) Date of Patent: Jul. 6, 2021

(54) ELECTRO KINETIC TRANSDERMAL AND TRANS MUCOSAL DELIVERY ACCELERATOR DEVICE

(71) Applicant: HG MEDICAL TECHNOLOGIES LLC, Fort Collins, CO (US)

(72) Inventor: Julian Henley, Fort Collins, CO (US)

(73) Assignee: HG MEDICAL TECHNOLOGIES LLC, Fort Collins, CO (US)

(*) Notice: Subject to any disclaimer, the term of this patent is extended or adjusted under 35 U.S.C. 154(b) by 48 days.

(21) Appl. No.: 16/008,366

(22) PCT Filed: Dec. 19, 2016

(86) PCT No.: PCT/US2016/067450
§ 371 (c)(1),
(2) Date: Jun. 14, 2018

(87) PCT Pub. No.: WO2017/106815
PCT Pub. Date: Jun. 22, 2017

(65) Prior Publication Data
US 2019/0151644 A1  May 23, 2019

Related U.S. Application Data

(60) Provisional application No. 62/268,816, filed on Dec. 17, 2015, provisional application No. 62/272,183, filed on Dec. 29, 2015.

(51) Int. Cl.
| | | |
|---|---|---|
| A61H 1/00 | (2006.01) |
| A61N 1/04 | (2006.01) |
| A61M 5/172 | (2006.01) |
| A61M 37/00 | (2006.01) |
| A61N 1/30 | (2006.01) |
| A61N 1/32 | (2006.01) |
| A61C 19/08 | (2006.01) |
| A61M 5/14 | (2006.01) |

(52) U.S. Cl.
CPC ........... *A61N 1/0428* (2013.01); *A61M 5/172* (2013.01); *A61M 37/00* (2013.01); *A61N 1/303* (2013.01); *A61N 1/325* (2013.01); *A61C 19/08* (2013.01); *A61M 5/14* (2013.01); *A61M 2037/0007* (2013.01); *A61N 1/044* (2013.01)

(58) Field of Classification Search
CPC .............. A61M 37/00; A61M 37/0092; A61M 2037/0007; A61N 1/30; A61N 1/303; A61N 1/325; A61N 1/0478
See application file for complete search history.

(56) References Cited

U.S. PATENT DOCUMENTS

| | | | |
|---|---|---|---|
| 7,520,875 B2 * | 4/2009 | Bernabei | A61H 7/008 604/20 |
| 2006/0058708 A1 * | 3/2006 | Heart | A61H 23/0245 601/2 |
| 2007/0250018 A1 * | 10/2007 | Adachi | A61M 37/0015 604/239 |

* cited by examiner

*Primary Examiner* — Laura A Bouchelle
(74) *Attorney, Agent, or Firm* — Riverside Law LLP

(57) ABSTRACT

A medical device for administering a medicament is disclosed that includes a reservoir for storing the medicament, a current driver electrically coupled to an electrode, and an oscillation driver electrically coupled to a vibrational element. The electrode forms multiple channels in fluid communication with the reservoir. A method of administering a medicament is also provided.

17 Claims, 10 Drawing Sheets

ELECTRO KINETIC TRANSDERMAL AND TRANS MUCOSAL DELIVERY ACCELERATOR DEVICE

CROSS-REFERENCE TO RELATED APPLICATIONS

This application is a national stage filing of International Application No. PCT/US16/67450 and claims priority to U.S. provisional application No. 62/272,183 filed on Dec. 29, 2015, and U.S. provisional application No. 62/268,816 filed on Dec. 17, 2015, all of which are incorporated herein by reference in their entireties.

BACKGROUND OF THE INVENTION

It has long been desirable to apply medication or other agents through skin, nail, or other biological tissue. This allows medication or other agents to be delivered more directly to affected topical surface areas and to targeted regions within a person's body. Delivering a drug across the skin or other tissue membrane, including transdermal or intradermal drug delivery, can also be advantageous in many applications where it is desirable to avoid problems associated with oral ingestion and drug delivery through the acidic environment of a stomach, or discomfort and hygienic issues involved in long needle delivery applications.

Various methods have evolved for applying medication or other agents across skin. Iontophoresis has been used as a way to apply medication locally through a patient's skin and to deliver medicaments to the eyes and ears. The application of an electric field to the skin is known to greatly enhance the skin's permeability to various ionic agents. The use of iontophoretic techniques has obviated the need for hypodermic injection of certain medicaments, thereby eliminating the concomitant problems of trauma, pain and risk of infection to the patient.

Iontophoresis involves the application of an electromotive force to drive or repel oppositely charged ions through the dermal layers into the area to be treated; either into the surrounding tissues for localized treatment or into the circulatory system for systemic treatment. Positively charged ions are driven into the skin at the anode while negatively charged ions are driven into the skin at the cathode. One readily observed benefit of transdermal iontophoretic drug delivery is the increased efficacy of the drugs delivered in this fashion. Studies have shown increased skin penetration of drugs at anodic or cathodic electrodes regardless of the predominant molecular ionic charge. This effect is mediated by polarization and osmotic effects. Regardless of the electrical charge on the medicament employed, two electrodes are used in conjunction with the patient's skin to form a closed circuit to promote the penetration or absorption of the medicament through the skin underlying the working electrode.

Iontophoretic devices are used to treat various conditions. For example, iontophoretic devices have been shown to effectively treat herpetic infection of the mucocutaneous junction. A number of studies demonstrate that a single line iontophoretic device and electrode design according to previously specified parameters has been efficacious in treating, and rapidly attenuating, a herpetic skin infection in humans with a single 3-10 minute application of an antiviral agent. Studies have also demonstrated that such a device is able to drive a significantly greater amount of Acyclovir into the dermis as compared to topical application of the antiviral agent. Such single line therapeutic devices apply an iontophoretic current and carry the therapeutic agent (in this particular case, Acyclovir), into the lesion where the herpes virus is replicating. This approach has proven itself, after numerous studies, to be greatly efficacious in effectively treating the viral herpetic infection at the mucocutaneous junction.

Different approaches have been used to further improve the performance of iontophoretic devices. One approach is to use a multi-line dispersive electrode. For example, U.S. Pat. No. 5,160,316 issued to Henley and incorporated herein by reference describes the use of a multi-line dispersive electrode. Each line is driven by separate electronic circuits to assure wide dispersion and enhanced penetration of medicament. Such wide field electrodes can not only cover a wide area of the body without succumbing to "tunneling effects", but they also provide sufficient skin penetration to function as a systemic drug delivery system. A second approach used to improve the performance of iontophoretic devices is to add ultrasonic elements to iontophoretic devices (this combination being referred to herein as ionosonic devices). For example, U.S. Pat. No. 5,658,247 issued to Henley and incorporated herein by reference describes a multi-line iontophoretic driver mounted on the application electrode with ultrasonic elements for enhanced intradermal delivery of therapeutic agents.

However, prior art ionosonic devices have various shortcomings. One limitation of the ionosonic design is the inefficiency of delivery of ultrasonic energy to the desired tissue surface. Sufficient energy should be supplied to the incorporated piezoelectric transducers to facilitate the electro kinetic transport. The electro kinetic energy is produced by the multi-line iontophoretic driver incorporated into the same application electrode. As the substance reservoir is interposed between the driver electrode and the neutral electrode, lateral to which is the piezoelectric source of energized ultrasonic compression wave, there are numerous reflective effects and inefficient impedance matching. Thus, the ultrasonic energy lacks significant enhancing effects making this configuration inefficient.

Thus, what is needed in the art is a device that allows for greater efficiency of electrode and ultrasonic energy transfer during medicament delivery.

SUMMARY OF THE INVENTION

In one embodiment, a medical device for administering a medicament includes a reservoir for storing the medicament; a current driver electrically coupled to an electrode; and an oscillation driver electrically coupled to a vibrational element; where the electrode forms a plurality of channels in fluid communication with the reservoir. In one embodiment, the vibrational element forms a portion of the plurality of channels. In one embodiment, the electrode and the vibrational element are in contact with each other. In one embodiment, the electrode forms a proximal portion of the plurality of channels and the vibrational element forms a distal portion of the plurality of channels. In one embodiment, the electrode is one of a plurality of electrodes. In one embodiment, each of the plurality of electrodes is independently driven by a corresponding current driver. In one embodiment, the electrode includes an insulation layer electrically insulating the electrode from the plurality of channels. In one embodiment, the electrode is detachable from the medical device. In one embodiment, the vibrational element is a piezo electric element. In one embodiment, the vibrational element is one of a plurality of vibrational elements. In one embodiment, a distal end of the vibrational element comprises a plurality of non-planar surfaces. In one embodiment, the oscillation driver is configured to vibrate the vibrational element at an ultrasonic frequency. In one embodiment, the medical device further comprises a ground electrode. In one embodiment, the ground electrode is coaxially disposed around a handle portion of the medical device. In one embodiment, the reservoir is an encapsulated unit dose. In one embodiment, the medical device includes a piercing element for rupturing the encapsulated unit dose. In one embodiment, the medical device is configured for rapid dental anesthesia and treatment of dental and mouth conditions, and each of the plurality of electrodes is independently driven by a corresponding current driver. In one embodiment, the medical device is configured for treatment of skin disorders by intradermal delivery, and each of the plurality of electrodes is independently driven by a corresponding current driver. In one embodiment, the medical device is configured for treatment of systemic conditions by rapid transdermal delivery of medication or therapeutic agent, and each of the plurality of electrodes is independently driven by a corresponding current driver. In one embodiment, a programmable controller is configured to control timing and delivery of therapeutic substances across tissue.

In one embodiment, a method of administering a medicament includes the steps of providing an electrode and a vibrational element that form a plurality of channels extending therethrough; positioning the vibrational element on or near a surface of a patient; and energizing the electrode and the vibrational element while simultaneously flowing a medicament through the plurality of channels. In one embodiment, the electrode is a plurality of electrodes, and the method includes independently driving the plurality of electrodes. In one embodiment, the vibrational element is energized to vibrate at an ultrasonic frequency. In one embodiment, the method includes actuating advancement of the medicament through the plurality of channels after the step of positioning.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION OF THE INVENTION

Figure 1A:
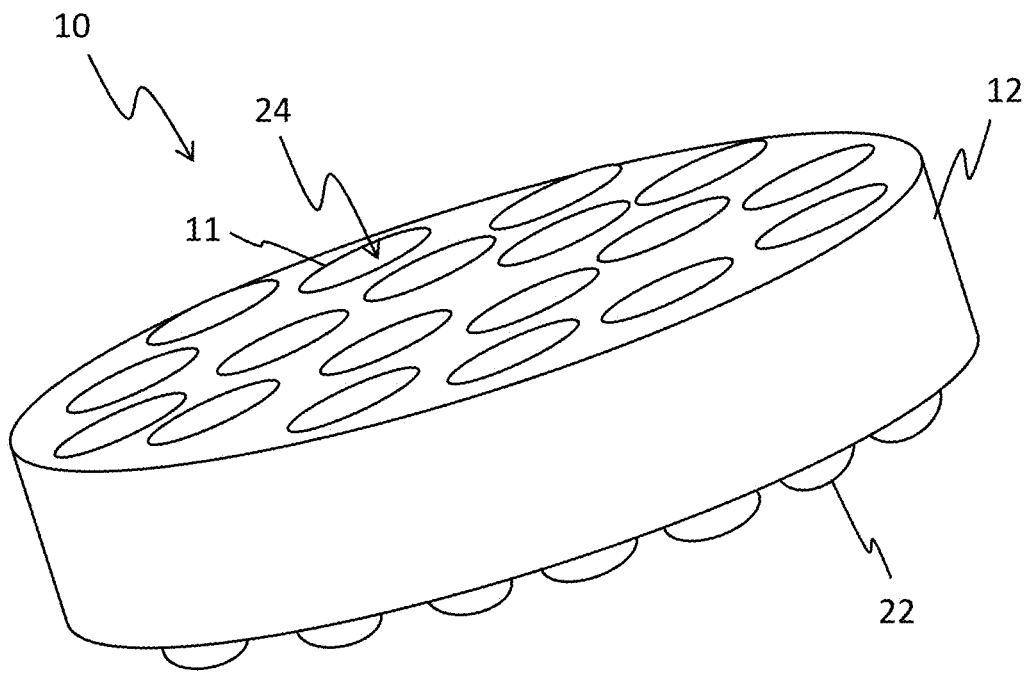
FIG. 1A is a perspective view and FIG. 1B is a cross-sectional view of an accelerator device according to one embodiment.

It is to be understood that the figures and descriptions of the present invention have been simplified to illustrate elements that are relevant for a more clear comprehension of the present invention, while eliminating, for the purpose of clarity, many other elements found in systems and methods of electro kinetic transdermal and trans mucosal delivery of medicament. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges: throughout this disclosure, various aspects of the invention can be presented in a range format. It should be understood that the description in range format is merely for convenience and brevity and should not be construed as an inflexible limitation on the scope of the invention. Where appropriate, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Referring now in detail to the drawings, in which like reference numerals indicate like parts or elements throughout the several views, in various embodiments, presented herein is an electro kinetic transdermal and transmucosal accelerator device.

Embodiments of the accelerator device described herein provide novel devices and methods utilizing ionosonic technologies having a ported electrode configuration. These delivery devices and methods can be used in a wide variety of embodiments and applications including, but not limited to, intradermal or transdermal delivery of one or more therapeutic agents toward or into a tissue (such as a skin, mucosa, or nail).

Figure 1B:
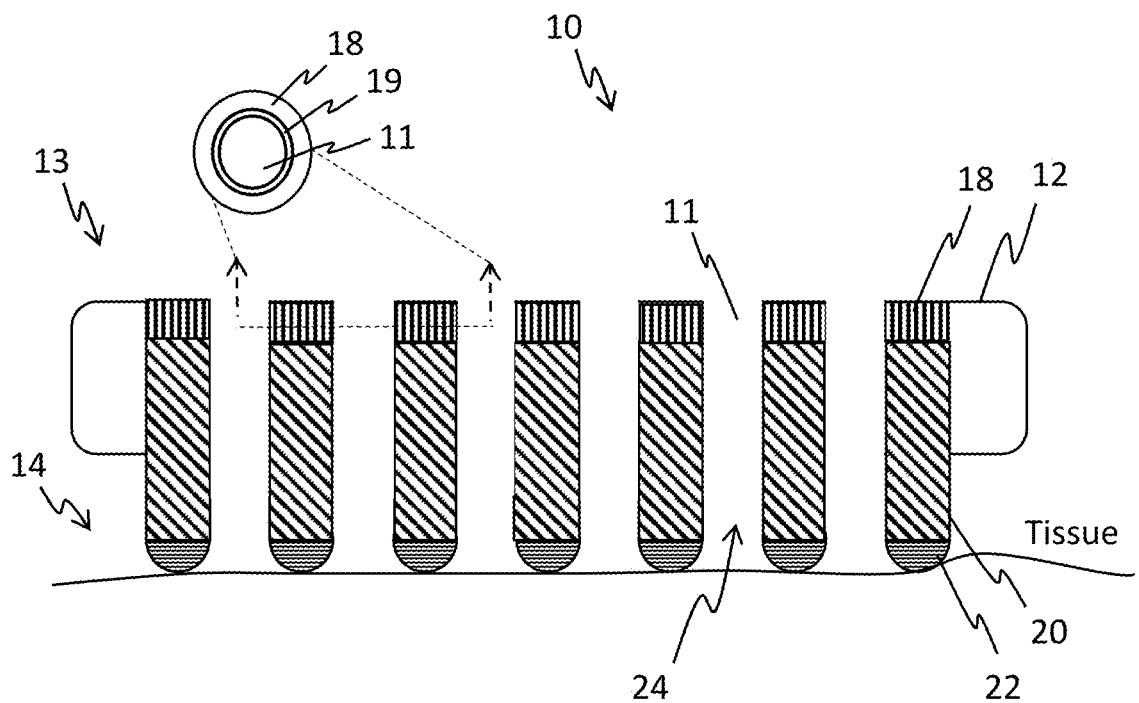

With reference now to FIGS. 1A and 1B, in one embodiment, an accelerator device 10 includes a housing 12, one or more electrode elements 18 and one or more vibrational elements 20. The electrode elements 18 and vibrational elements 20 are arranged with openings that form multiple ports 11, each having a channel 24 extending between proximal end 13 and distal end 14 of the device 10. The ports 11 form micro channels incorporated into the electrode element 18 and the vibrational element 20. In certain embodiments, the electrode element 18 is a single electrode, and in other embodiments, the electrode element 18 is multiple electrode elements operating on independent drive signals. Embodiments may use for example, 1-3 electrodes and drive signals, 4-11 electrodes and drive signals, 12-24 electrodes and drive signals, or more than 24 electrodes and drive signals. In smaller applications, a single iontophoretic electrode can be sufficient. For wider areas and to prevent "current tunneling" effects and blistering, multiple iontophoretically energized electrodes can be used such that each electrode is controlled by an independent current driver and limiter. In certain embodiments, each electrode overlying a multiplicity of ports can vary its voltage automatically until a specified flow current is reached within the area of its control and distribution. Advantageously, unlike prior contact electrodes, the accelerator device according to the various embodiments can be used for extended periods with externally applied treatment agents, and have fewer Ph-associated issues.

In one embodiment, the vibrational element 20 is a piezo electric element. The vibrational element 20 can be structured to have direct vibrational contact with target tissue by use of geometric structural projections 22 between the ports 11. In certain embodiments, the vibrational elements 20 terminate inrounded or corrugated ends 22 that contact the tissue to increase patient comfort and surface contact with the tissue. The rounded or corrugated ends 22 can be an extension of the vibrational elements or a can be made of a separate material. The ends can otherwise utilize short irregularities, non-sharp irregularities, projections or lattices. Such structure improves the coupling of the vibratory component, decreases vibratory transmission problems, and converts many of the vertical mode oscillations into multi-mode coupling which improves molecular transport across the electrode tissue boundary. Irregular or non-planar projected boundaries can be manufactured as separate adherent layer against the piezo material, or it can be etched into the piezo material itself or deposited upon such.

In certain embodiments, the device 10 is designed so that when in use, the ports 11 are saturated with a desired medicament that is in electrical contact with an overlying dispersive single or multi-line array of iontophoretic electrode elements 18. In certain embodiments, the iontophoretic electrode elements 18 are electrically isolated from the ports 11 by an insulation layer 19 (see FIG. 1B) so as not to decrease the efficiency of the device 10. The insulation layer 19 can prevent leak current through the conductive ports 11 through which medicament resides and is transported electro kinetically to the encountered tissue. In certain embodiments, such as for example embodiments implemented in smaller hand held devices, there is no insulation layer where the piezo driver electrode and iontophoretic electrode are combined into one by using DC offset or diode rectification of the piezo signal. In these cases, the piezo driver electrode can be in electrical contact with the ports and the medicament therein.

Figure 2:
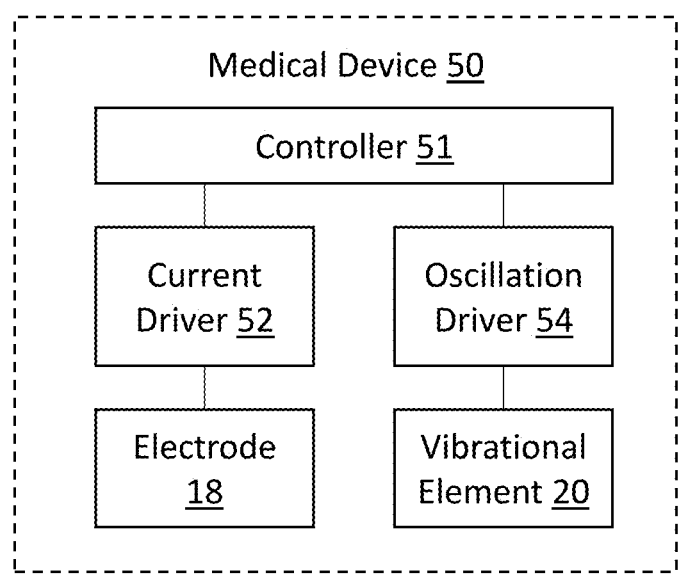
FIG. 2 is a system diagram of an accelerator device according to one embodiment.

In certain embodiments, as shown in the system diagram of FIG. 2, the accelerator device 10 is a component of a medical device 50 and is operationally driven by a controller 51. The controller 51 regulates signals to the current driver 52 which drives power to the electrode 18, and to the oscillation driver 54 which provides the oscillation signal for the vibrational element. In one embodiment, the controller 51 is part of the medical device 50. In other embodiments, the controller 51 is a separate component that is communicatively coupled (e.g., hard wired or wirelessly) to the current driver 52 and oscillation driver 54. The current driver 52 and oscillation driver 54 can be part of the medical device 50 or for example be part of equipment in the medical suite that attaches to the medical device 50. In certain embodiments, the controller can be configured to control timing and delivery of therapeutic substances across tissue.

Figure 3A:
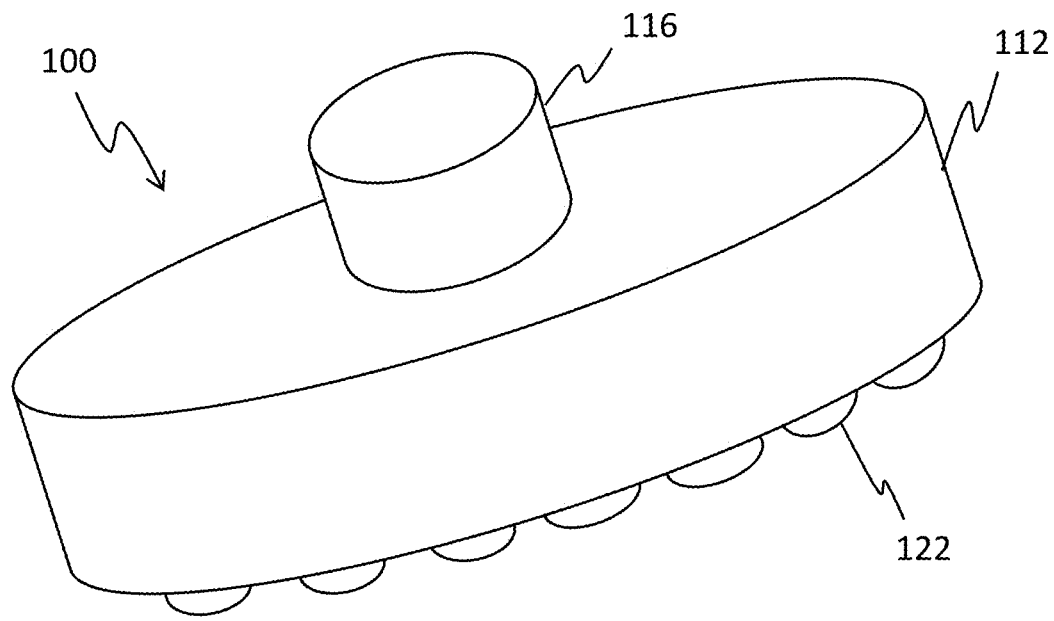
FIG. 3A is a perspective view and FIG. 3B is a cross-sectional view of an accelerator device according to one embodiment.
Figure 3B:
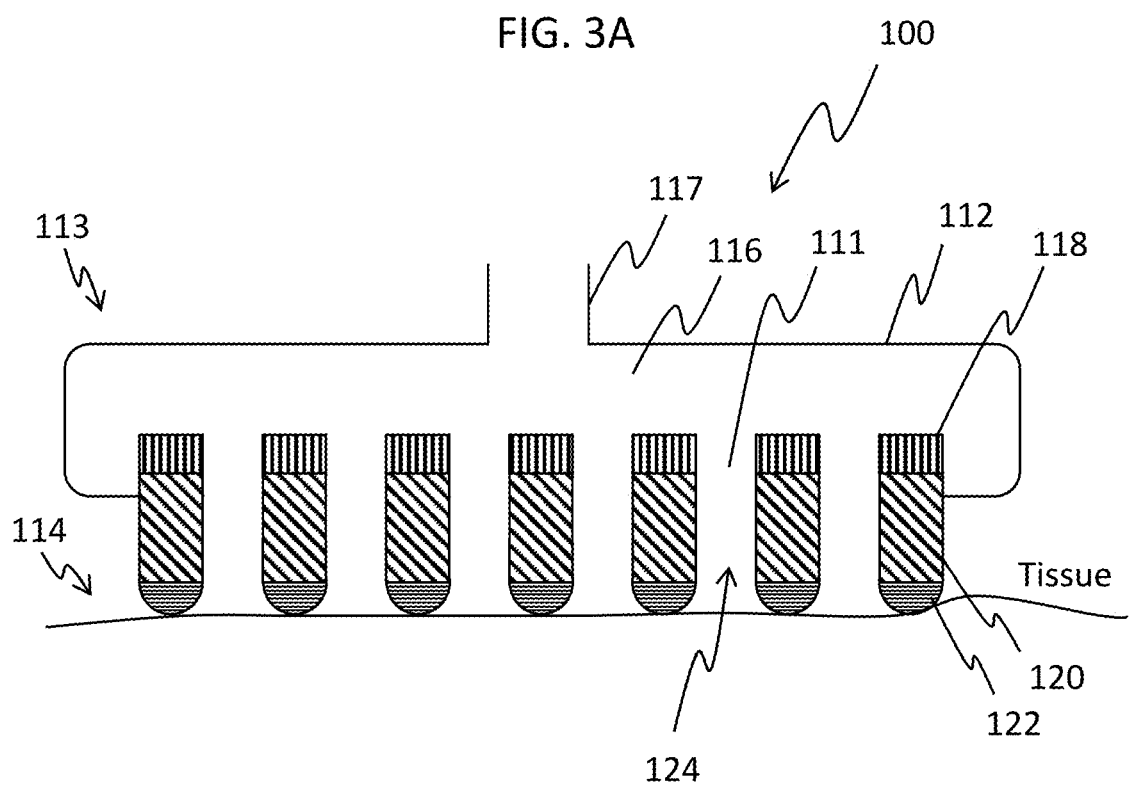

The configuration of the electrode and vibrational elements can take various geometric forms and have various port layouts as shown for example in the various embodiments. As shown in the embodiment of FIGS. 1A and 1B, the ports can extend the entire height of the accelerator device 10. With reference now to FIG. 3B, an accelerator device 100 is shown that has a filler cap 117 on a proximal end 113 that is in fluid communication with a reservoir 116 for supplying medicament to the ports 111 and channels 124. The reservoir 116 is formed by the housing 112 that secures the electrode 118 and vibrational 120 elements. The channels 124 terminate distally 114 in rounded edges similar to the embodiment of FIGS. 1A and 1B. In one embodiment, the housing 112 is arranged to support one or more piezoelectric vibrational elements 120 with incorporated port and/or microchannel elements within the piezo electric assembly, as well as the plurality of iontophoresis electrodes 118. In one embodiment, the iontophoresis electrodes 118 are imbedded within a housing support member.

In certain embodiments, the iontophoresis electrodes are arranged at or near respective groups of microchannels. The electrodes can operate off of a single signal or multiple independent signals. In a multi-signal embodiment, each iontophoresis electrode can be separated and electrically isolated from the other electrode(s). Each of a plurality of current drivers can be coupled to each of their respective iontophoresis electrodes. In this way, each iontophoresis electrode has a separate electrical signal driven by a corresponding current driver.

In the various embodiments, such as those of FIGS. 1A-3B, the medication flows through the multiple ports. In certain embodiments, the medication is pushed distally both by a multi-line dispersion electrode which can be photo-etched, and is further pumped by the vibrational effects of the vibrational element forming the ports. The dispersion iontophoretic electrodes will preferably be directly photo-etched on the outer surface of the piezo electric elements or can be photo-etched upon a malar film which is than adhered to the outer surface of the piezo electric element. In certain embodiments, the vibrational elements are piezoelectric elements coupled to the iontophoretic multi-line electrode and to the flow ports as an integral assembly allowing for the direct coupling of the ultrasonic energy directly to the desired tissue. The multiple ports and their incorporating matrix move and vibrate the tissue in response to the changes in the vibrational piezoelectric elements. Electrical current can be applied to the plurality of iontophoresis electrodes to further drive the agent toward the targeted portion of the mammal's body. Such electromechanical coupling between the ported vibrational element, and the iontophoretic electrode elements jointly effect the penetration to a greater degree than any of the components separately. Such combined coupling of the aforementioned technologies working together and concurrently on an applicator electrode lead to delivery flux benefits that are greater and more efficacious than any of the technologies working alone or separately. In certain embodiments, the port channels have different internal diameters. In certain embodiment, the port channels have the same internal diameters. The port channels can be interspersed between the plurality of iontophoretic driver electrodes in a uniform or non-uniform fashion.

Figure 4A:
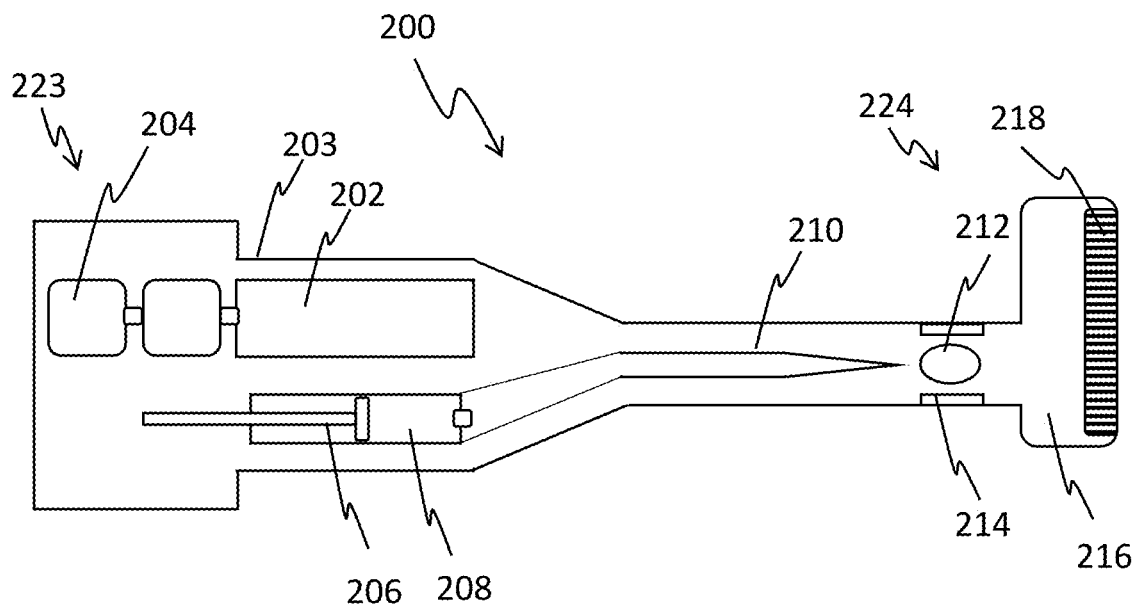
FIG. 4A is a schematic view and FIG. 4B is a magnified schematic view of an applicator according to one embodiment.
Figure 4B:
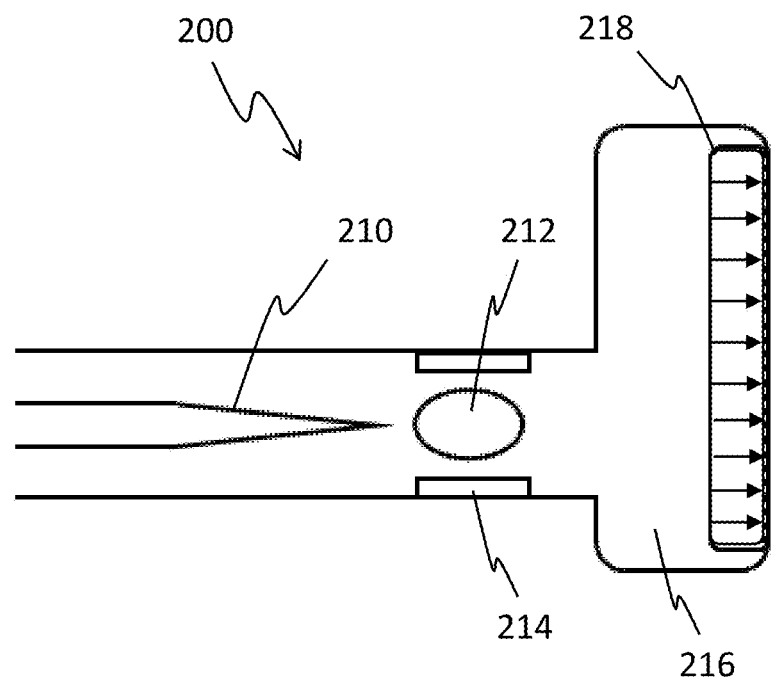

With reference now to FIGS. 4A and 4B, an applicator 200 is shown according to one embodiment. The proximal end 223 of the applicator 200 includes batteries 204 and a controller 202 in the handle. The outer shell 203 serves not only as handle but also as grounding counter electrode to the active iontophoretic electrode of the accelerator device 218 located at the active tip. The ported iontophoretic electrode and the vibratory element, such as a ported piezo vibratory portion, can be configured similarly to the ported accelerator devices of FIGS. 1A-3B. The contact portion containing the accelerator device and its small container shell at a distal end 224 of the applicator can be a disposable plug in cap with pin electrical connectors. A small reservoir 208 having a plunger 206 can be prefilled with an inert polymer rupturable unit containing medicament formulated for optimal ionosonic penetration. In certain embodiments, a pin 210 is used to pierce the embedded medicament unit dose capsule 212 secured by a chamber 214 at a distal end 224 of the device 200 to allow the medication to contact the accelerator device 218. The device 200 can be activated upon loading the unit dose and the whole system of activation is therefore performed by one manual action of inserting the active tip upon the driver handle and applying the activated device to desired tissue area. A number of polymer encapsulating materials known in the art that can be used to contain the unit dose, such as polyethylene, polypropylene, Mylar, and Teflon. These materials are inert and offer rupturability combined with long shelf life within the applicator electrode by virtue of chemically inert encapsulation.

Figure 5:
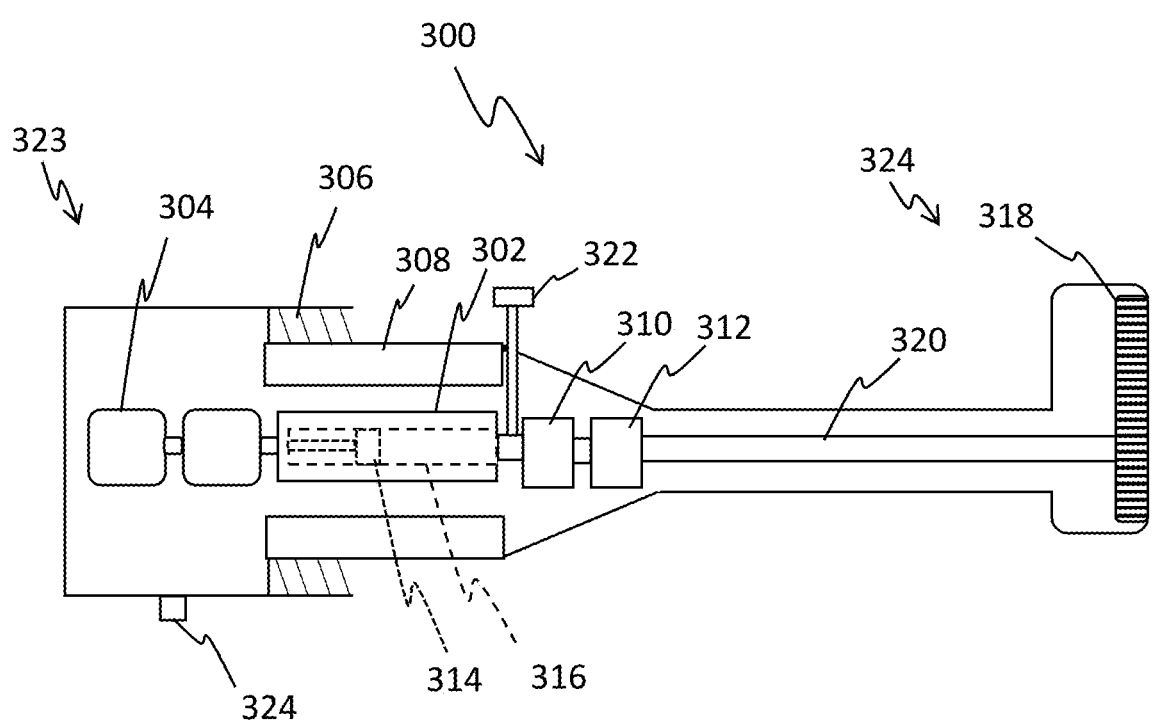
FIG. 5 is a schematic view of an applicator according to one embodiment.

With reference now to FIG. 5, an applicator 300 is shown according in one embodiment. The proximal end 323 of the applicator 300 includes batteries 304 and a controller 302 in the handle. The outer shell 308 doubles as handle and a grounding counter electrode to the active iontophoretic electrode of the accelerator device 318 located at the active distal end 324 of the applicator 300. The ported iontophoretic electrode and the vibratory element, such as a ported piezo vibratory portion, can be configured similarly to the ported accelerator devices of FIGS. 1A-3B. A small reservoir 316 having a plunger 314 is centrally located in the handle next to the controller 302. A threaded portion 306 is used to detach and attach the proximal end 323 of the handle to access the batteries 304, the controller 302 and the reservoir 316 components. An access port 322 can also be used to access the reservoir 316. Medicament can be advanced from the reservoir 302 via the plunger 314 and down the conduit 320 to the accelerator device 318.

In certain embodiments, an agent can be included in a medicament. In one embodiment, the medicament includes a natural plant derived agent that is not classified as a pharmaceutical, such as morselized tobacco leaf as a source of nicotine, alcohol as solvent, or dmso (Dimethyl Solfoxide—CH3(SO)) as a carrier/solvent. The medicament can be included in the applicator as part of a separate medicament layer, as part of the support member, as part of the ported assembly, or applied externally to the exterior of the ported iontophoretic-vibrational assembly. In one embodiment the medicament is transmitted into the ports and dispersed among the projecting portions of the piezo electric elements in contact with the tissue. In certain embodiments, the agent is released or moved when the piezo electric ported membrane or similar elements move and vibrate tissue in contact with the applicator in response to the at least one piezoelectric element, and when electrical current is applied to the plurality of iontophoresis electrodes to further drive the agent toward the targeted portion of the mammal's body.

Embodiments of the accelerator devices incorporated into an applicator can be a portable pen-like device can be readily available for use to drive a medicament, such as acyclovir or IUDR, into the target area on the body, such as early herpetic lesions. With the accelerator device, the treatment efficacy will be greatly multiplied beyond known devices.

In one embodiment, an ionosonic intradermal drug delivery device incorporating the accelerator device is adapted to releasably attach to a mammal's body so that a skin-contacting surface of the device is adjacent to a targeted portion of the mammal's skin, mucosa, or nail. The device is operable for ionosonically driving a medicament across a skin/tissue contacting surface of the device into a targeted portion of the mammal's skin, mucosa, gingiva, tissue or nail. The device includes a medicament carrying layer in fluid communication with the skin-contacting surface of the device and a porous sheet impregnated with a medicament containing fluid. In one embodiment, hand held devices can be used in treatment of mucocutaneous herpes with acyclovir, Valtrex, or IUDR.

In one embodiment, flow ports are created through the piezoelectric material by utilizing piezoelectric crystal, wafer, or membrane and subjecting it to scanned laser for creation of micro channels. This will allow for flow of a medicament through the piezo electric layer directly to the tissue surface which is subject to the vibrational forces transmitted directly via the underside of the peizoelectric material and is also in direct contact with the tissue floating upon a thin layer of vibrationally dispersed medicament. As illustrated in FIGS. 1A-1B and 3A-3B, the tissue contact portion of the ported piezoelectric elements can have rounded projections to further improve the vibrational transfer from the accelerator device to contiguous tissue, creating a micro cavitation effect on the tissue boundary and making it significantly more porous. This better controls the iontophoretic push exerted by the integrated iontophoretic dispersion electrodes.

The iontophoretic drive signal can be combined with a high frequency wave drive of the piezoelectric elements upon a single or multiple dispersion signals by superimposition of a DC offset upon the waveform and isolating the patient ground from the piezoelectric drive waveform. In some embodiments, the waveform is a square wave but other waveforms are also useful. An alternate method of using the piezoelectric waveform not only to create the vibrational state of the electrode but also to supply the iontophoretic drive by means of integrated diode waveform filtration is possible and may be more useful for miniaturized lower cost/disposable applications. In certain embodiments, separate connector electrodes will deliver the waveform to the piezoelectric elements and separate single or multi-line connector electrodes will deliver iontophoretic drive currents.

Figure 6A:
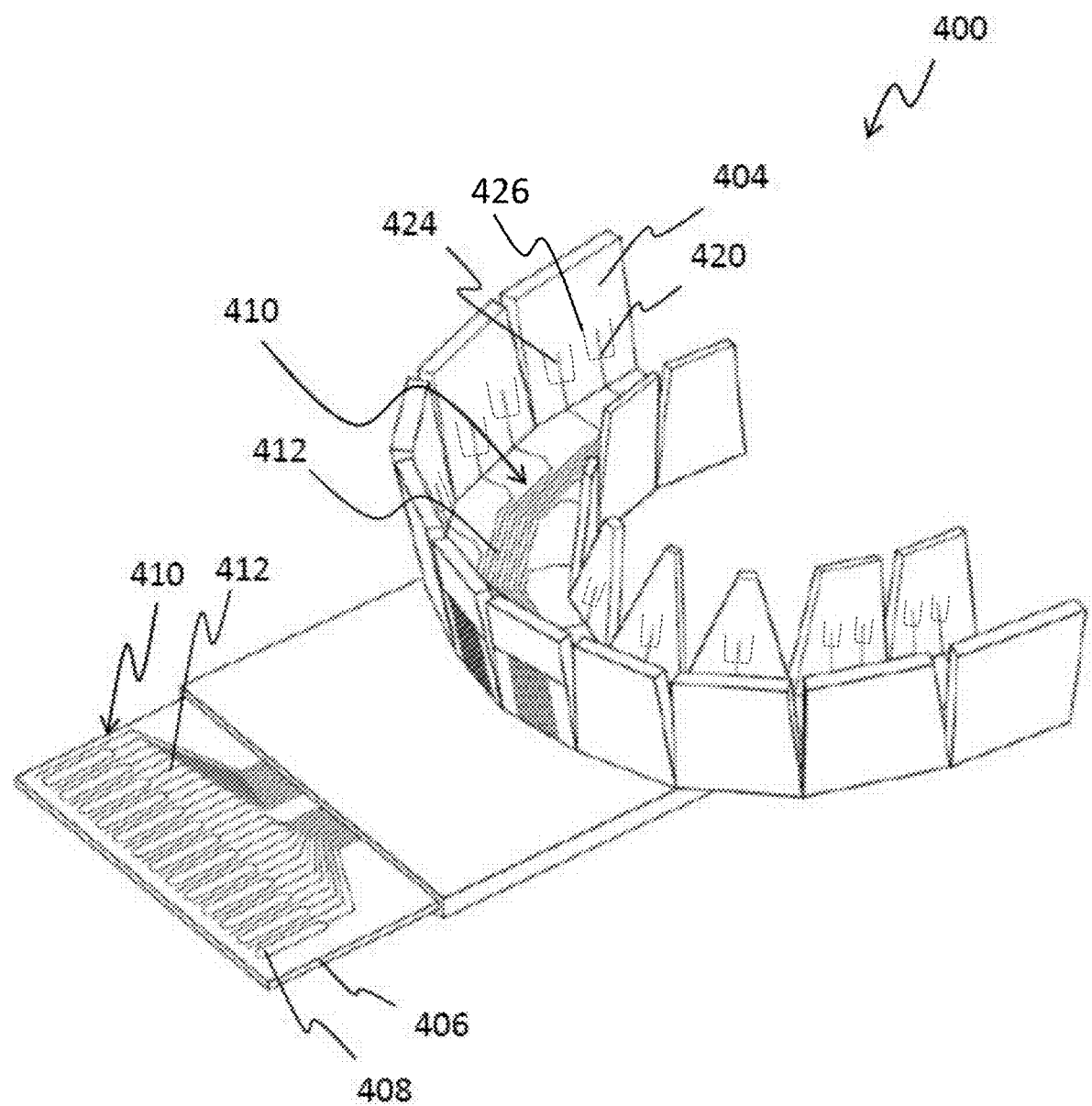
FIG. 6A is a perspective view and FIG. 6B is a top view of a dental applicator having branched electrodes according to one embodiment.
Figure 6B:
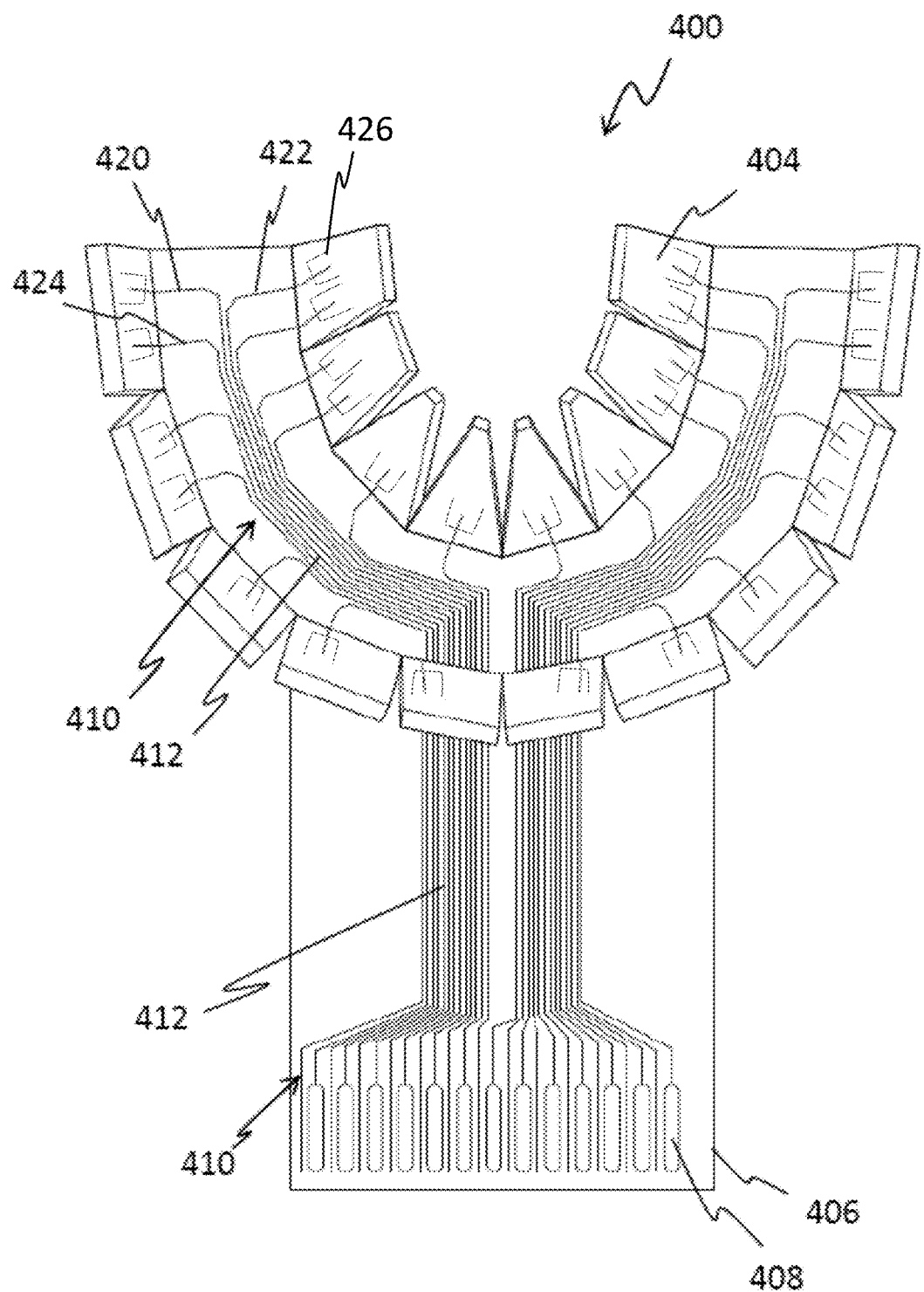
Figure 6C:
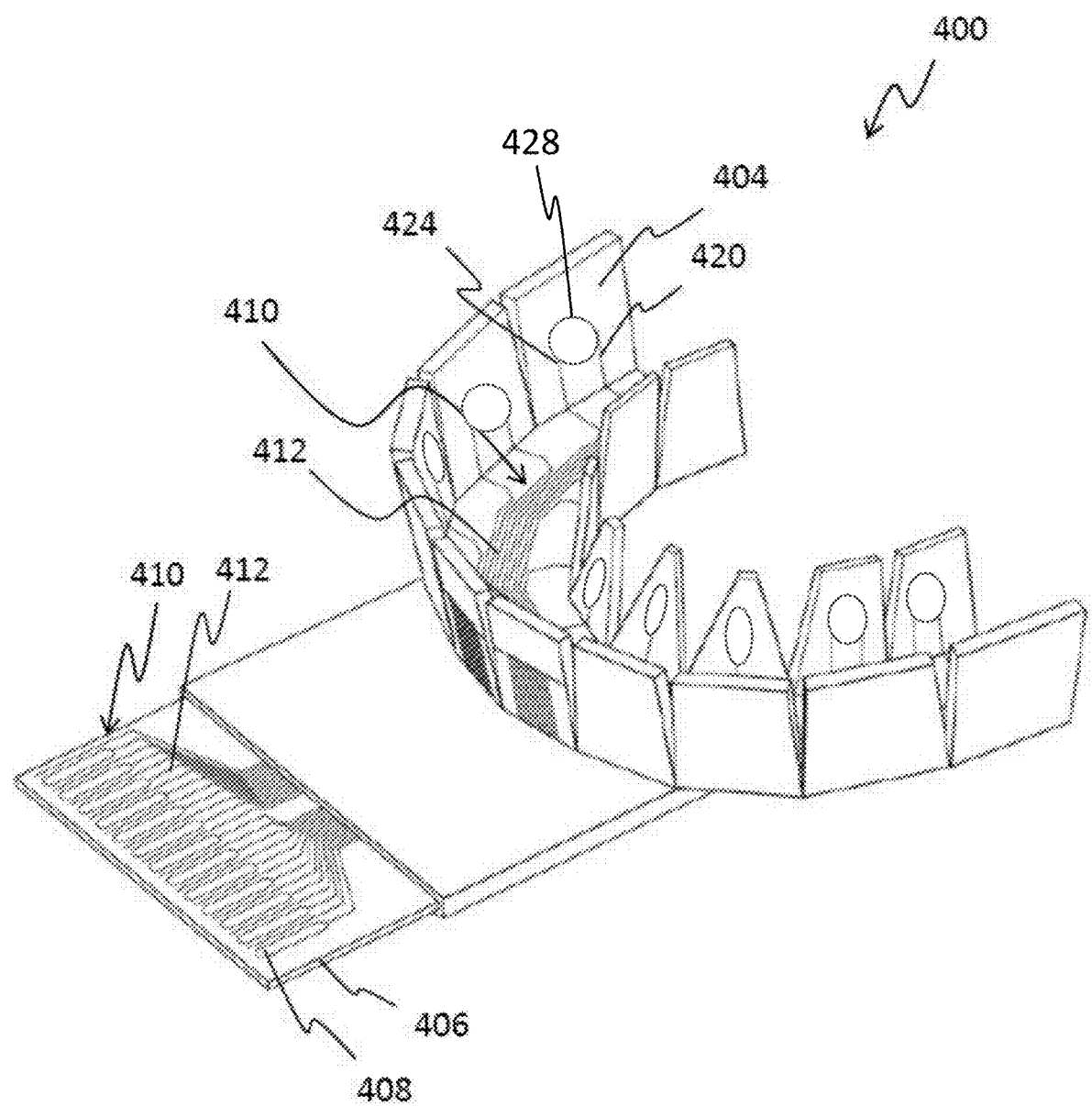
FIG. 6C is a perspective view and FIG. 6D is a top view of a dental applicator having ported ionosonic elements according to one embodiment.
Figure 6D:
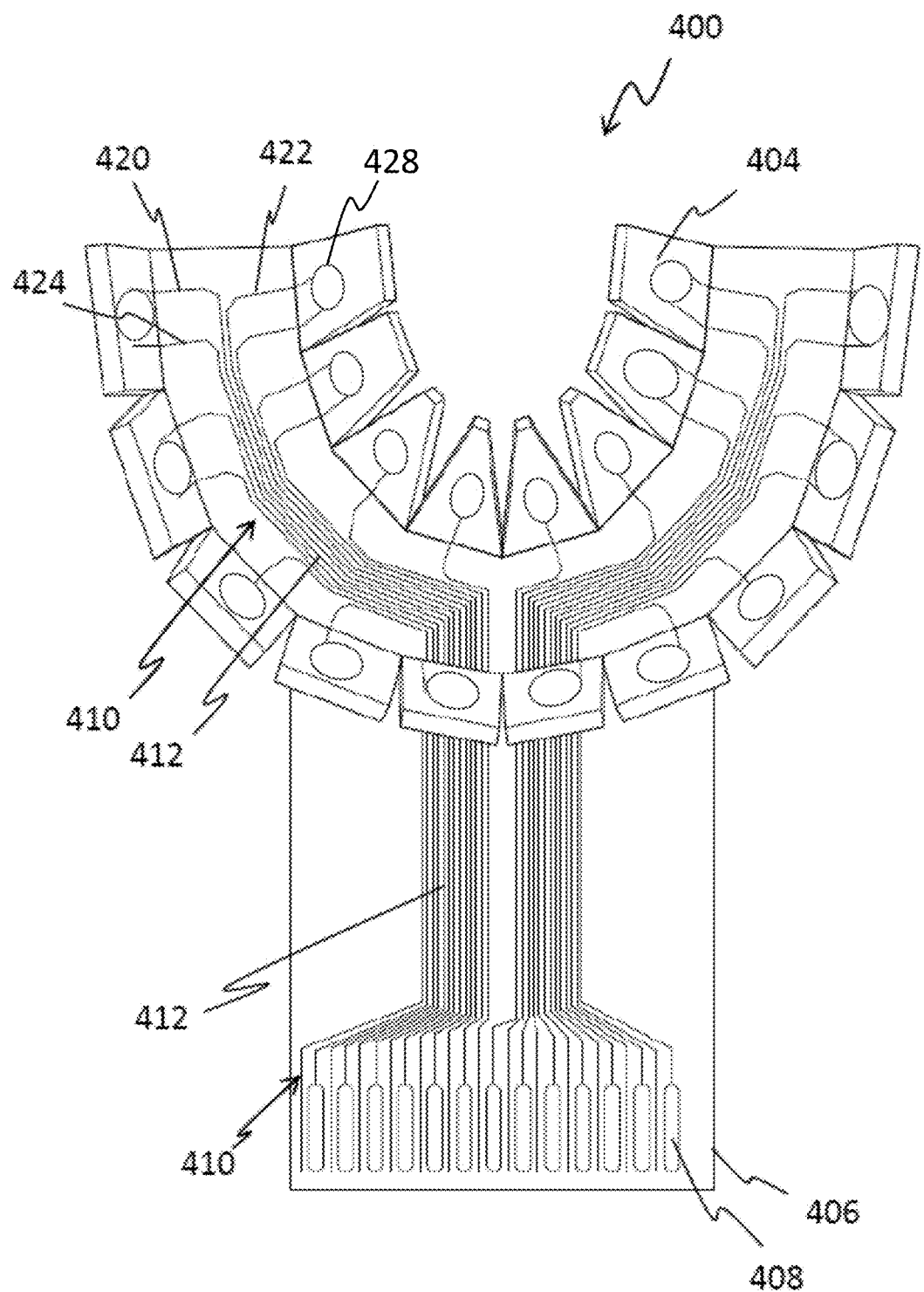

One of several exemplary devices that can utilize the accelerator electrode is a device to achieve rapid dental anesthesia. Common outpatient dental procedures often involve injectable blocks of anesthesia to control the procedure pain. OSHA recommends use of none injectable devices if such are made available and work reliably and effectively. Issues of needle injuries both to health workers and patients underlie the OSHA recommendation. An effective non injectable alternative device is not yet available. Accordingly, the accelerator device can be adapted for use in a dental applicator 400 as shown in the embodiments of FIGS. 6A-6D. The dental applicator 400 has an electrode 410 that in certain embodiments is formed on a flexible sheet as a multi-line conductive matrix 412. The conductive matrix 412 distributes current on a tissue contacting surface thereof, such as a metallic foil, a conductive rubber or resin film, a carbon film or other conductive coating or electro dispersive material. The conductive matrix 412 is flexible so that it may be contoured to the interior surfaces 404 of the dental applicator 400. Embodiments of the dental applicator can be used with or without the ported ionosonic elements described herein. In one embodiment, a medicament can be applied to the interior surfaces 404 of the dental applicator 400 directly onto the conductive matrix 412. In one embodiment, a separate medicament-carrying layer formed from a porous material can be attached to the conductive matrix 412, for example by an adhesive. With reference specifically to the embodiment shown in FIGS. 6A and 6B, the line wires of the conductive matrix 412 can terminate in a dispersive tree 426 at each flap. The dispersive tree 426 can have 2, 3, 4, 5 or more branches as needed to achieve the desired dispersion pattern. The branches can form a symmetrical or asymmetrical pattern, with branches having different lengths and geometries. Certain flaps (such as for example larger flaps) can have more branches than others, and trees from flap to flap need not be uniform. Branches can include curved portions, straight portions, or combinations of the two. One or more branches can split into two or more additional branches, and so on. In one embodiment, the dispersive tree 426 covers an area of ¼ to 1 cm squared. In one embodiment, the dispersive tree 426 covers an area of ½ to ¾ cm squared. In one embodiment, each dispersive tree 426 is connected in parallel. In one embodiment, two or more sets of dispersive trees 426 are connected to independently controlled power sources. With reference specifically to FIG. 6B, in one embodiment, an active electrode line 420 can be positioned opposite a ground electrode line 422. In one embodiment, an active electrode line 420 can be positioned adjacent to a ground electrode line 424. In one embodiment, various combinations of oppositely and adjacently opposed electrodes can be utilized. In one embodiment, the entire conductive matrix 412 is an active electrode and grounding electrodes are employed to cover a similar area near the active electrode, such as a skin ground electrode pad. In one embodiment, with reference specifically to FIGS. 6C and 6D, ported ionosonic elements 428 as described herein are positioned at each dental flap for tissue contact. In one embodiment, the ported ionosonic elements 428 are energized by two etched conductors connected in series with each other. As shown in FIGS. 6C and 6D, line connections can both be at the surface, or one or more connections can be below the surface or behind the ionosonic element 428. In one embodiment, the ionophoretic terminals are connected in parallel as described in the previous embodiment. The ported ionosonic elements 428 can be circular or oval as shown. The ported ionosonic elements 428 can also have a flat edge geometry, such as rectangular or trapezoidal.

A ribbon connector can be used to connect an electrical power source to an electrode connection element 406 and to deliver the electrical current by means of the multi-connectors 408 to the line wires of the conductive matrix 412. In certain embodiments, each wire in the matrix carries no more than 1 milliamp of current. The amount of current that flows to each line is controlled by a control circuit to prevent a tunneling effect from occurring as is known in the art. Each lead wire in the conductive matrix 412 can be electrically driven simultaneously or in a sequential multiplex manner. The use of simultaneous or parallel electrical current to each lead wire in the array would be employed, for example, in the application of medicament to burns where a wide area of dispersion is required. Multi-line embodiments for the various devices described herein can be implemented in a manner similar to the dental applicator 400.

A partial bite tray configuration with a multi-line driver will effectively anesthetize several teeth at once. A full upper or combined upper maxillary and lower mandibular tray can rapidly anesthetize the sensitive gingiva with delivered, for example, pontocaine, xylocaine, cetacaine or related topical anesthetic agents. Such gingival anesthesia can be helpful for common procedures like dental cleaning, scaling, and periodontal procedures. The same delivery configuration can be used to treat refractory gingivitis and associated halitosis by virtue of driving appropriate antibiotic and anti-inflammatory agents into the recessed gingival retracted pockets where the tooth destructive inflammatory process continues unabated and leads to the most common cause of loss of teeth. This potentially can become a viable treatment and or preventive modality for periodontal disease.

Figure 7:
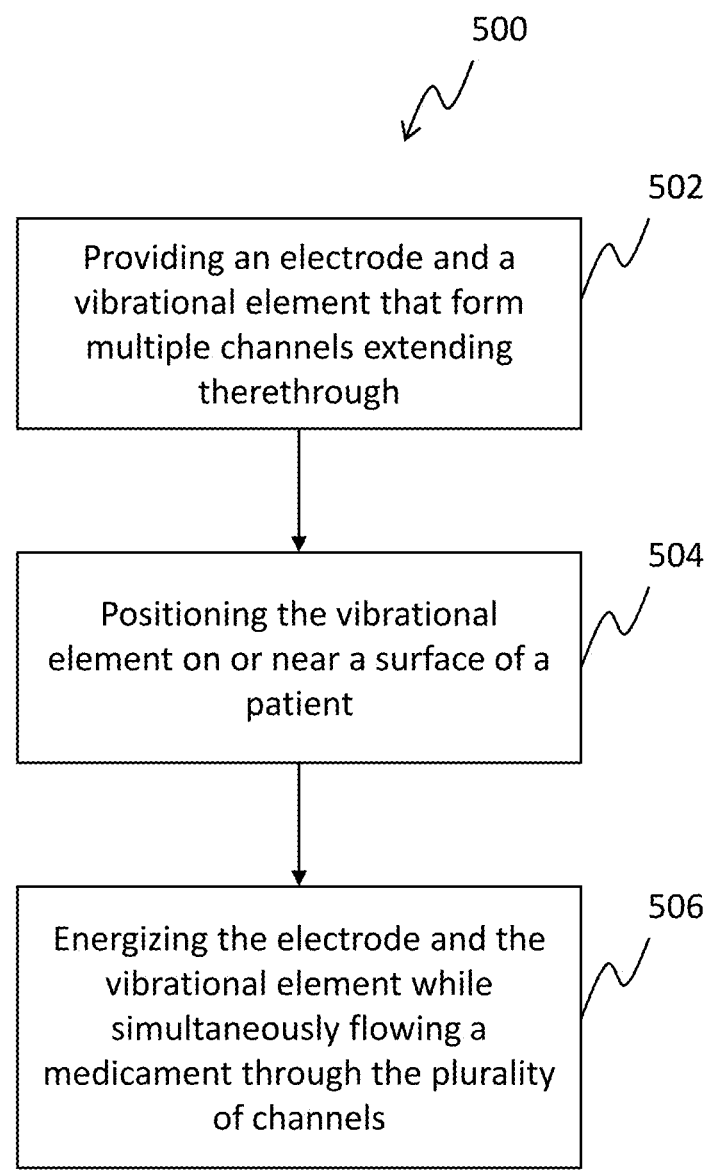
FIG. 7 is a method of administering a medicament according to one embodiment.

With reference now to FIG. 7, according to one embodiment, a method 500 of administering a medicament is provided. The method includes the steps of providing an electrode and a vibrational element that form multiple channels extending therethrough 502, positioning the vibrational element on or near a surface of a patient 504, and energizing the electrode and the vibrational element while simultaneously flowing a medicament through the plurality of channels 506. In one embodiment, the electrode is a plurality of electrodes, the method includes the step of independently driving the plurality of electrodes. In one embodiment, the vibrational element is energized to vibrate at an ultrasonic frequency. In one embodiment, the method includes the step of actuating advancement of the medicament through the plurality of channels after the step of positioning.

Various categories of medical devices that rely on iontophoresis, single channel, multichannel, and ionosonic electrokinetic approaches can be modified to utilize the acceleration device. Embodiments can include ported electrode elements in certain embodiments, and can additionally include ported vibrational elements in certain embodiments.

In one embodiment, a gloved configuration such as that described in U.S. Pat. No. 6,895,271 to Henley and incorporated herein by reference is implemented for effective self-application of medicament to wider areas such as acne, or for massage, pain attenuation, or cosmeceuticals. In one embodiment, a sock configuration such as that described in U.S. Pat. No. 6,477,410 to Henley et al. and incorporated herein by reference can utilize the ported ionosonic elements described herein for treatment of fungal infestations between the toes can also utilizes the ported ionosonic elements described herein.

In one embodiment, a smokeless cigarette configuration such as that described in U.S. Pat. No. 5,331,979 to Henley and incorporated by reference is implemented that delivers nicotine via mouthpiece contact, which can also be programmed as an effective smoking cessation device with incorporation of biofeedback. Incorporation of the accelerator device makes it more effective than prior technology, and now makes it competitive with vapor alternatives that use the lung for transport and are associated with yet not well understood health hazards. This embodiment results in a more efficacious and functional device by implementing it with the new accelerator device technology.

In one embodiment, a programmable wrist band configuration such as that described in U.S. Pat. No. 6,148,231 to Henley and incorporated herein by reference utilizes the ported ionosonic elements described herein. Embodiments of the programmable wrist band configuration can be implemented for delivery of medicament to treat BP and cardio tropic issues. The device can have an integrated feedback loop to deliver systemic targeted medication as needed. In one embodiment, the device delivers trans dermal antihypertensive medication only when BP goes above a certain threshold, rather than having the patient thrown into hypotension by a conventional average daily dose approach. In one embodiment, a programmable pain management and release configuration can be implemented and set with daily limits and intelligent transdermal delivery worn around the wrist like watch or on another part of the body. A form of transdermal Fentanyl patch with intelligent time and limit modulation. It is clear that pain comes in waves and is should be treated as such.

In one embodiment, a lip shaper device with the appearance and feel of existing lipstick applicator is implemented, such as that shown in U.S. Pat. No. 6,735,470 to Henley et al. and incorporated herein by reference. The device features the enhanced capability of temporarily enlarging/engorging the lip as alternative to painful cosmetic injections of foreign substances. In one embodiment, naturally occurring osmotic loaders, vasoactive vegetable oils and substances found in our daily food supply are used as the medicament In one embodiment, a face mask applicator is implemented, such as that described in U.S. Pat. No. 6,792,306 to Henley et al and incorporated herein by reference. The face mask achieves the purpose of skin hydration and wrinkle attenuation by means of an accelerator device and enhanced driver that amplifies the cosmetic function of cosmeceuticals. The device also drives in neuropraxic agents such as botox and dysport to treat dynamic contracture of muscles of facial expression that contribute to formation of rhydities.

In one embodiment, a head cap similar to a swimming cap is implemented to utilize the accelerator device. Wide field inophoretic and ionosonic principles are implemented for the treatment of baldness by driving in substantial levels of medicament into the hair bearing area that modulates hair growth such as exemplified by minoxidil and Latisse. Because the accelerator device drives medicament preferentially into the atrophic hair roots, the device constructed in accordance with designs described herein has unique capability of amplifying the biological agents that either amplify or attenuate hair growth. Accordingly, the device fills a specific clinical need for which few functional options are available at this time. Embodiments of the device provide a low level iontophoretic and/or iontosonic trickle delivery of agent affecting hair growth. Agents can include for example Minoxidil, Latanoprost, Bimatoprost, Fluridil, Ketoconazple, Spironolactone, Melatonin, and topical estradiols. The device can also provide for treatment of Alopecia Aerata (autoimmune hair loss) with immunological agents such as Tofacitinib and related JAK inhibitors. JAK inhibitors are a type of medication that functions by inhibiting the activity of one or more of the Janus kinase family of enzymes (JAK1, JAK2, JAK3, TYK2), thereby interfering with the JAK-STAT signaling pathway. These inhibitors have therapeutic application that includes treatment for hair loss. JAK inhibitors may include for example, Ruxolitinib (INCB018424), Tofacitinib (CP-690550) Citrate, AZD1480, Fedratinib (SAR302503, TG101348), AT9283, AG-490 (Tyrphostin B42), Momelotinib (CYT387), Tofacitinib (CP-690550, Tasocitinib), WP1066, TG101209, Gandotinib (LY2784544), NVP-BSK805 2HCl, Baricitinib (LY3009104, INCB028050), AZ 960, CEP-33779, Pacritinib (SB1518), WHI-P154, XL019, S-Ruxolitinib (INCB018424), ZM 39923 HCl, Decernotinib (VX-509), Cerdulatinib (PRT062070, PRT2070), Filgotinib (GLPG0634), FLLL32, BMS-911543, Peficitinib (ASP015K, JNJ-54781532), GLPG0634 analogue, Go6976 and Curcumol.

In one embodiment, a hand held pen-like portable wireless device utilizes the accelerator device to achieve rapid localized tissue anesthesia in preparation of blood draw, i.v. placement, deeper nerve block, or deep tissue biopsy. Embodiments of the device achieve localized skin/tissue anesthesia in a short time (for example, about 60 seconds) and significantly attenuate skin or tissue penetration with an injectable needle that is often associated with greater pain and apprehension. A variety of skin applicator configurations for the treatment of skin fungal and nail fungal infestations can be implemented. The ported channels can act as a secondary treating reservoir for the slow release of an antifungal agent. In certain embodiments, reservoirs are only partially enclosed, such as for example on two or three sides.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention.

What is claimed is:

1. A medical device for administering a medicament comprising:
a reservoir for storing the medicament;
a current driver electrically coupled to an electrode; and
an oscillation driver electrically coupled to a vibrational element, a distal end of the vibrational element comprising a non-planar surface;
wherein the electrode forms at least one channel in fluid communication with the reservoir, the channel terminating distally within a structural projection configured on a distal surface of the device.

2. The medical device of claim 1, wherein the electrode forms a plurality of channels in fluid communication with the reservoir.

3. The medical device of claim 2, wherein the vibrational element forms a portion of the plurality of channels.

4. The medical device of claim 1, wherein the electrode and the vibrational element are in contact with each other.

5. The medical device of claim 1, wherein the electrode forms a proximal portion of the at least one channel and the vibrational element forms a distal portion of the at least one channel.

6. The medical device of claim 1, wherein the electrode is one of a plurality of electrodes that form a plurality of channels in fluid communication with the reservoir.

7. The medical device of claim 6, wherein each of the plurality of electrodes is independently driven by a corresponding current driver.

8. The medical device of claim 1, wherein the electrode includes an insulation layer electrically insulating the electrode from the at least one channel.

9. The medical device of claim 1, wherein the electrode is detachable from the medical device.

10. The medical device of claim 1, wherein the vibrational element is a piezoelectric element.

11. The medical device of claim 1, wherein the oscillation driver is configured to vibrate the vibrational element at an ultrasonic frequency.

12. The medical device of claim 1, further comprising a programmable controller configured to control timing and delivery of therapeutic substances across tissue.

13. A method of administering a medicament comprising:
   providing an electrode and a vibrational element that form at least one channel extending therethrough, a distal end of the vibrational element comprising a non-planar surface, the channel terminating distally within a structural projection configured on a distal surface of the device;
   positioning the vibrational element on or near a surface of a patient; and
   energizing the electrode and the vibrational element while simultaneously transmitting a medicament through the at least one channel.

14. The method of claim 13, wherein the electrode and vibrational element form a plurality of channels extending therethrough, and wherein the step of energizing comprises simultaneously transmitting a medicament through the plurality of channels.

15. The method of claim 13, wherein the electrode is a plurality of electrodes, the method further comprising:
   independently driving each of the plurality of electrodes.

16. The method of claim 13 further comprising:
   actuating transmission of the medicament through the plurality of channels after the step of positioning.

17. A medical device for administering a medicament comprising:
   a reservoir for storing the medicament;
   a current driver electrically coupled to an electrode; and
   an oscillation driver electrically coupled to a vibrational element;
   wherein the electrode forms at least one channel in fluid communication with the reservoir, the channel terminating distally within a structural projection configured on a distal surface of the device, and
   wherein the electrode is detachable from the medical device.

* * * * *